United States Patent [19]

Shah

[11] Patent Number: 4,642,119
[45] Date of Patent: Feb. 10, 1987

[54] CONNECTIVE TISSUE PROSTHESIS

[75] Inventor: Jitendera S. Shah, Bristol, England

[73] Assignee: Johnson & Johnson, New Brunswick, N.J.

[21] Appl. No.: 755,237

[22] Filed: Jul. 15, 1985

[30] Foreign Application Priority Data

Jul. 16, 1984 [GB] United Kingdom ............. 8418018

[51] Int. Cl.$^4$ .............................................. A61F 2/08
[52] U.S. Cl. ................................................... 623/13
[58] Field of Search ................................ 623/13, 1, 66

[56] References Cited

U.S. PATENT DOCUMENTS

| | | | |
|---|---|---|---|
| 3,842,441 | 10/1974 | Kaiser | 623/13 |
| 3,987,497 | 11/1976 | Stoy et al. | 623/13 |
| 4,187,558 | 2/1980 | Dahlen et al. | 623/13 |
| 4,301,551 | 11/1981 | Dore et al. | 623/13 |
| 4,321,711 | 3/1982 | Mano | 623/1 |
| 4,584,722 | 4/1986 | Levy et al. | 623/13 |

FOREIGN PATENT DOCUMENTS 0106501  4/1984  European Pat. Off. ............. 623/13

Primary Examiner—Richard J. Apley
Assistant Examiner—Alan W. Cannon

[57] ABSTRACT

A prosthesis, such as a ligament or tendon prosthesis, comprises a low elastic modulus load bearing element (1) to which are attached a plurality of fine filaments (3) having a higher elastic modulus. The arrangement is such that the fine filaments are unstressed unless the load on the prosthesis exceeds a predetermined value, thus simulating the mechanical response of native collagenous tissue. The fine filaments, which are preferably of polyester, are arranged to allow ingrowth of fresh connective tissue.

16 Claims, 8 Drawing Figures

CONNECTIVE TISSUE PROSTHESIS

This invention relates to a connective tissue prosthesis, and in particular to a prosthesis for use in place of a natural ligament or tendon.

Numerous different constructions have been proposed for tendon and ligament prostheses. Early proposals were generally for prostheses in the form of a single load bearing element of a biocompatible material, and such constructions continue to be proposed. While such prostheses usually have the requisite tensile strength, their behaviour is very different from that of native collagenous soft tissue, because they display a substantially constant modulus of elasticity over a wide range of applied tensile loads. In contrast, a natural ligament or tendon displays a comparatively low modulus of elasticity under low tensile loads, and a greatly increased elastic modulus under high tensile loads. This means that natural ligaments and tendons are sufficiently resilient to provide enough movement to minimise the strain imposed on the connection with bone or soft tissue, but sufficiently resistant to large stresses to avoid excessive, and thus damaging, movement of joints.

Attempts have been made to produce prostheses which more closely mimic the mechanical properties of natural collagenous tissue. For example, British Patent Specification No. 1471837 discloses a tendon prosthesis consisting of a core and of a sheath. The preferred core consists of a knitted fabric or twisted fabric bundle embedded in an elastic oriented polymer. It is said that such a core gives a performance similar to that of a genuine tendon, and the prosthesis as a whole is said to be "physiologically inert".

More recently, the trend has been towards prostheses which are not physiologically inert, but which on the contrary, elicit the positive physiological response of fibrogenesis. Such a prosthesis is described in British Patent Specification No. 1602834. However, this prosthesis, being formed from a single material, suffers the same disadvantages as the earlier prior art prostheses as regards the nature of its response to the increasing load.

The present invention seeks to provide an implantable prosthesis with a mechanical response similar to that of native soft collagenous connective tissues, which is moreover capable of promoting a considerable degree of collagen fibrogenesis.

According to the present invention there is provided a biocompatible connective tissue prosthesis, comprising a first load bearing element and a bundle of fine filaments which are arranged to allow ingrowth of connective tissue, said filaments being of higher elastic modulus than the effective elastic modulus of the first element, and being attached to the first element at spaced points along their length, the length of filament between said points being greater than the unstressed length of the first element between said points, such that the filaments are substantially unstressed unless the load on the prosthesis exceeds a predetermined value.

Thus, in contrast to the prosthesis disclosed in Specification No. 1471837, the high modulus material is available to be intertwined with collagen, following ingrowth of new tissue. We have found that the high modulus material should not be completely surrounded by the low modulus material (such as is the case in the prosthesis disclosed in Specification No. 1471837), because low modulus materials in general do not promote fibrogenesis.

The prosthesis of the present invention is capable of non-linear elastic deformation so that a comparatively large elastic stretch is obtained on the application of low tensile forces, but greatly increased forces produce comparatively little further deformation. Furthermore, in contrast to the prosthesis disclosed in Specification No. 1471837, there is substantially no shear interaction between the materials of different elastic modulus when the prosthesis is stretched as a whole.

The material or materials used in the prosthesis according to the invention must be biocompatible in the sense of inducing no adverse biological reaction, and being well tolerated by fibroblasts. It is also preferable that the material or materials are readily sterilizable by commonly used methods such as $\gamma$-irradiation, autoclaving and ethylene oxide treatment.

Preferably, the first load bearing element has an effective elastic modulus of from 0.1 to 2 MPa, for example 0.5 to 1.5 MPa, and the filaments preferably have a collective elastic modulus of from 100 to 3000 MPa, for example 1000 to 2000 MPa. The particular elastic modulus chosen for the first element and the filaments will depend on the use to which the prosthesis is to be put. For example, a prosthesis for use in a child will generally have a lower elastic modulus than a prosthesis for use in an adult, because connective tissue of children is generally more elastic than that of adults.

The term "effective elastic modulus", as used in relation to the first element, means the elastic modulus of the first element as a whole. This elastic modulus may be derived from the inherent properties of the material from which it is made. Thus, for example, the first element may comprise one or more substantially straight filaments of the desired elastic modulus, such as medical grade silicone rubber.

In an alternative construction, the first element derives its effective elastic modulus not merely from the elastic modulus from which it is made, but also from the conformation in which this material is arranged. Thus, the first element may be in the form of a spring, such as a coil spring, of a material which has a relatively large elastic modulus, the desired elastic modulus being that of the spring as a whole.

The linear elastic strain limit of the first element will generally be greater than 20%, while the linear elastic strain limit of the filaments is preferably at least 2 to 3%.

It will be appreciated that the mechanical response of the prosthesis of the invention can be made to suit individual requirements not only by choosing materials having the desired elastic modulus and elastic strain limit, but also by varying the length of the filaments between the points of their attachment to the first element, relative to the relaxed length of the first element between those points. Generally, the fine filaments will be of such a length relative to the first element that the maximum degree to which the first element can be stretched without stressing the filaments is in the range 1 to 15%, and more preferably in the range 1 to 5%.

The prosthesis may be in the form of an elongate ligament or tendon prosthesis. Such a prosthesis is designed to bear tensile stresses essentially in a single direction, and may be referred to as a "one-dimensional" prosthesis. It will be understood, however, that the invention is equally applicable to two-, or even three-dimensional prostheses, i.e. to prostheses which are designed to bear stresses in two or three mutually perpendicular directions. Moreover, a ligament or tendon prosthesis may, if desired, be branched, the mechanical properties of each branch being tailored to match the mechanical properties of the branched ligament or tendon which the prosthesis is designed to replace.

The fine filaments will generally be formed from a plastics material, such as a polyester or polyamide, for example nylon. A ligament or tendon prosthesis according to the invention preferably comprises from 50 to 1500 yarns, each consisting of from 20 to 100 fine filaments. The number of fine filaments to be used in any prosthesis depends on the overall strength, elastic modulus, cross sectional area and extent of elastic stretch required of the prosthesis, and on the corresponding properties of the individual fine filaments. The fine filaments preferably have a diameter in the range 8 to 20 microns.

When the fine filaments are provided in the form of filamentary yarns, these may be twisted or braided. In any such construction, however, care must be taken to ensure that the fine filaments are not so tightly packed that ingrowth of fresh collagenous tissue is prevented. The packing density of the fine filaments should preferably be slightly lower than that given by a close packed hexagonal arrangement of fine filaments.

The fibrogenicity of the prosthesis may be further enhanced by coating the fine filaments with agents which promote infiltration and adhesion, such as fibronactin and/or heparin The prosthesis may be sterilised, for example by gamma-irradiation, and may be hermetically sealed in a sterile envelope. One or both ends of the fine filaments may be collectively threaded through a surgical needle, so that the prosthesis is immediately ready for use by the surgeon.

The present invention also provides a method of making the prosthesis described above, the method comprising stretching a first load bearing element by a predetermined amount and then fixing a bundle of filaments at two or more spaced points along the length of the first element, such that the filaments are unstressed unless the first element is stretched by said predetermined amount.

A prosthesis according to the invention, and a method of making such a prosthesis, are now disclosed, by way of example, with reference to the accompanying drawings, in which.

Figure 1:
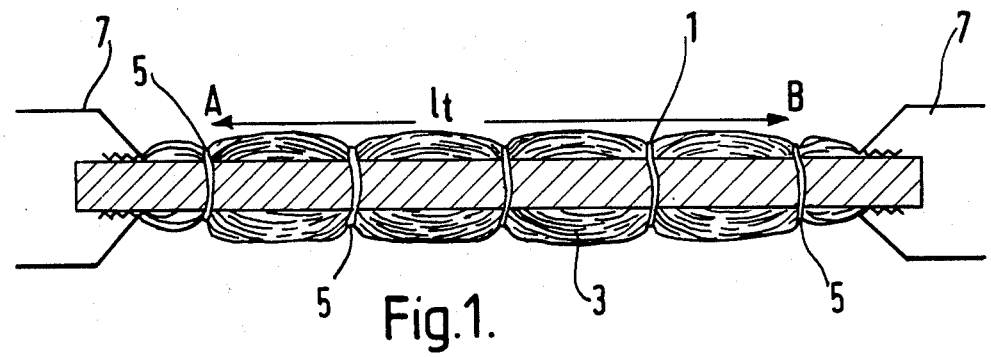
FIG. 1 is a schematic view of a prosthesis in a partially stretched state.
Figure 2:
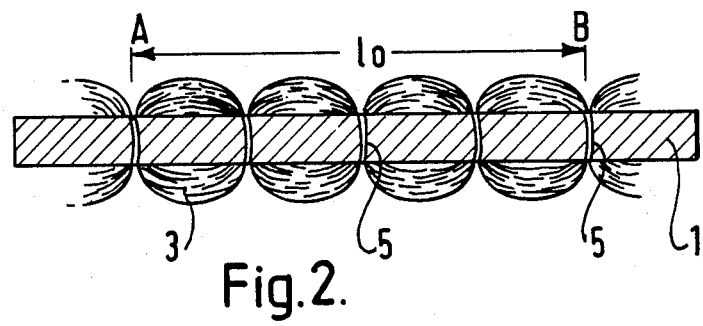
FIG. 2 is a schematic view of the prosthesis of FIG. 1 in a relaxed state.

Referring to the drawings, a ligament prosthesis comprises a first load bearing element 1 in the form of a relatively thick silicone monofilament (e.g. SILASTIC silicone monofilament made by Dow Corning. SILASTIC is a Trade Mark). A bundle of fine polyester filaments 3, of 10 micron diameter, are connected to the first load bearing element 1 at spaced intervals as indicated at 5.

The prosthesis is made as follows. The silicone monofilament 1, after washing in a detergent solution, is clamped between two clamps 7 and stretched so that the distance between two marker points AB is increased from the rest length $1_o$ to the desired stretched length $1_t$. Fine filaments of polyester of length greater than $1_t$ are then washed in detergent solution and laid around the pre-stretched silicone, and fastened to the silicone at the points 5. Fastening can be effected by using non-toxic biologically tolerable glue, surgical staples or by typing with additional yarns of polyester. The fine polyester filaments 3 should be unstressed at this stage, as shown in FIG. 1.

After the fine polyester filaments 3 are suitably attached to the silicone monofilament 1, the prosthesis is removed from the clamps, so that a distance AB reverts to $1_o$.

In use, the elastic modulus of the prosthesis at small deformation is given by the elastic modulus of the silicone monofilament, since the fine polyester filaments are unstressed. As the deformation of the prosthesis increases so that the length AB exceeds $1_t$, the elastic modulus of the prosthesis is given essentially by the elastic modulus of the fine polyester filaments. This is illustrated graphically in FIG. 3.

Figure 3:
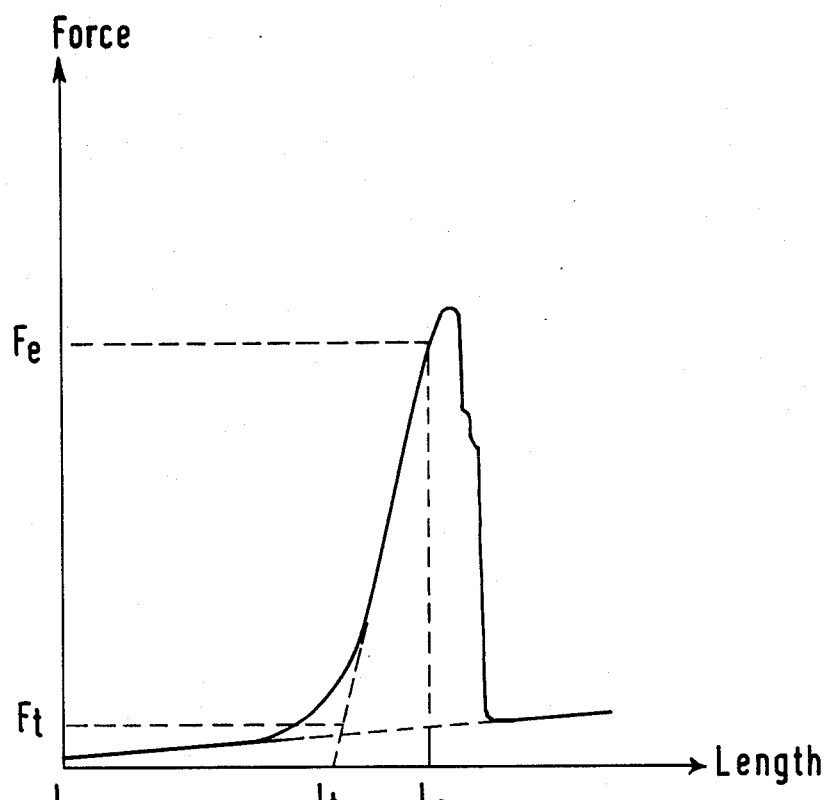
FIG. 3 is a graph showing the stress/strain curve of the prosthesis of FIG. 1.

As FIG. 3 shows, applying an increasing tensile force to the prosthesis gives a comparatively large, and essentially linear increase in length of the prosthesis until the force reaches a value $F_t$. This is the force required to stretch the distance between the markers AB from $1_o$ to $1_t$.

As the applied force is increased, the fine filaments begin to stretch, and the stress/strain curve shows a transition from the low modulus linear response given by the first element, to the higher modulus, essentially linear response given by the fine filaments. This higher modulus linear response is seen until the applied force reaches $F_e$, at which point the length AB is given by $1_e$, the linear elastic limit of the fine filaments. Increasing the applied force still further produces non-elastic deformation of the prosthesis, and then ultimate failure. It is therefore preferable to construct the prosthesis so that in use it is never stretched beyond the length $1_e$.

Figure 4:
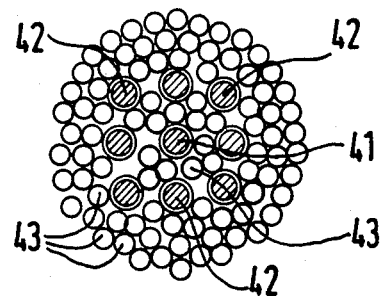
FIGS. 4 and 5 show schematic sections through alternative constructions of prosthesis.

It is not necessary for the first load bearing element to be constituted by a single monofilament or for such a monofilament to be located at the centre of the bundle of fine filaments. A plurality of elements of circular, rectangular, square or other cross sections may be dispersed among the fine filaments. For example, FIG. 4 illustrates a section through a ligament prosthesis in which the first load bearing element is constituted by a central SILASTIC monofilament 41 and eight further SILASTIC monofilaments 42 disposed equiangularly around the central monofilament. Fine polyester filaments 43 are arranged not only around the eight monofilaments 42, but also between these latter and the central monofilament 41.

Figure 5:
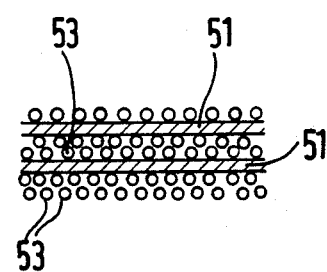

FIG. 5 shows a section through a prosthesis in which the first load bearing element is constituted by two sheets of SILASTIC silicone rubber 51, in a layered arrangement with fine polyester filaments 53.

Figure 6:
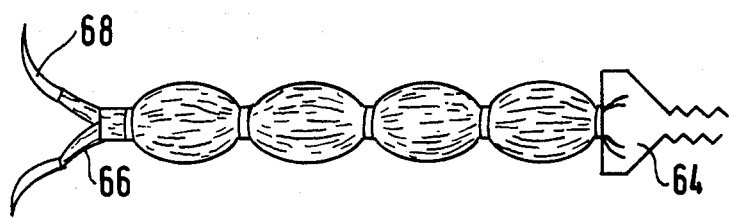
FIG. 6 shows a prosthesis provided with needles for suturing.

As shown in FIG. 6, the ends of the prosthesis may be inserted or fixed in connectors 64 to facilitate threading and fixation in surgical procedures. Alternatively, one or both ends of the protruding silicone monofilament may be cut off and the fine filament ends 66 prepared ready for suturing with surgical needles 68.

Figure 7:
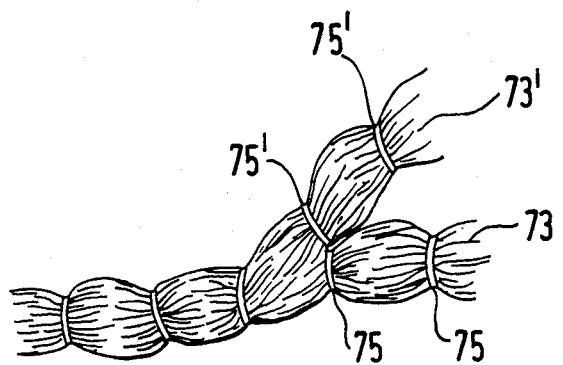
FIG. 7 illustrates a branched prosthesis.
Figure 8:
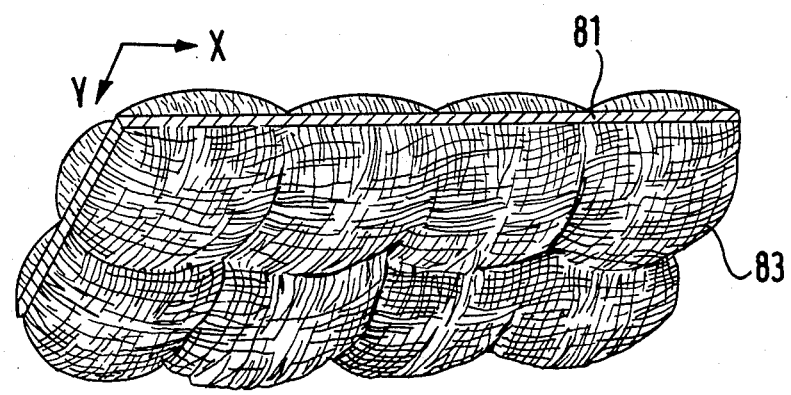
FIG. 8 shows a prosthesis adapted for receiving a load in two mutually perpendicular directions.

In the embodiment shown in FIG. 7, the first load bearing element (not shown) is branched, with some of the fine filaments 73 being attached to one branch at 75, and other fine filaments 73' being attached to the other branch at 75'. The length of the fine filaments between the points 75, and the number of such filaments, need not necessarily be the same as the length and number of fine filaments between the points 75', so that the two branches display different mechanical properties, For replacement of tissues which bear biaxial stresses, the form shown in FIG. 8 may be adopted. In this construction the first load bearing element comprises a membrane 81 of low elastic modulus material which is pre-stretched in two mutually perpendicular directions (represented by X and Y) before attaching two crossed but distinct sets of fine filaments which are oriented respectively in the X and Y directions.

I claim:

1. A bio-compatible connective tissue prosthesis, capable of non linear deformation comprising a first load bearing element, and a bundle of fine filaments which are arranged to allow ingrowth of connective tissue, said filaments having a collective elastic modulus which is greater than the effective elastic modulus of the first element, and being directly attached to the first element at spaced points along their length, the length of filament between said spaced points being greater than the unstressed length of the first element between said spaced points, such that the filaments are substantially unstressed unless the load on the prosthesis exceeds a predetermined value.

2. A prosthesis according to claim 1 wherein the first load bearing element has an elastic modulus of from 0.1 to 2 MPa.

3. A prosthesis according to claim 1 wherein the fine filaments have a collective elastic modulus of from 100 to 3,000 MPa.

4. A prosthesis according to claim 1 wherein the elastic strain limit of the first element is substantially greater than that of the fine filaments.

5. A prosthesis according to claim 1 wherein the linear elastic strain limit of the fine filaments is from 2% to 3%.

6. A prosthesis according to claim 1 wherein the maximum degree to which the first element can be stretched without stressing the fine filaments is in the range 1% to 15%.

7. A prosthesis according to claim 1 wherein the first element comprises a single core, and is surrounded by the fine filaments.

8. A prosthesis according to claim 3 wherein the first element is in the form of a spring having the required elastic modulus.

9. A prosthesis according to claim 1 wherein the first element comprises one or more substantially straight filaments.

10. A prosthesis according to claim 9 wherein the first element is a medical grade silicone rubber filament.

11. A prosthesis according to claim 1 wherein the fine filaments are of a polyester or polyamide, and have a diameter in the range 8 to 20 microns.

12. A prosthesis according to claim 11 comprising from 50 to 1500 filamentary yarns, each consisting of from 20 to 100 fine filaments.

13. A prosthesis according to claim 1 wherein one or both ends of the fine filaments are threaded through a surgical needle.

14. A prosthesis according to claim 1 wherein the fine filaments are wound or woven around the first element.

15. A prosthesis according to claim 14 wherein the fine filaments are coated with an agent promoting cell adhesion.

16. A method of making a prosthesis comprises stretching a first load bearing element by a predetermined amount and then fixing a bundle of fine filaments at two or more spaced points along the length of the first element, such that the fine filaments are unstressed unless the first element is stretched by said predetermined amount.

* * * * *

UNITED STATES PATENT AND TRADEMARK OFFICE
CERTIFICATE OF CORRECTION

PATENT NO. : 4,642,119

DATED : February 10, 1987

INVENTOR(S) : Jitendera S. Shah

It is certified that error appears in the above-identified patent and that said Letters Patent is hereby corrected as shown below:

Claim 16 should be deleted from the patent.

On the Title Page, "16 Claims, 8 Drawing Figures" should read
-- 15 Claims, 8 Drawing Figures --.

Signed and Sealed this

First Day of March, 1988

Attest:

DONALD J. QUIGG

*Attesting Officer*  *Commissioner of Patents and Trademarks*